United States Patent [19]

Mano et al.

[11] E Patent Number: Re. 31,618

[45] Reissued Date of Patent: Jul. 3, 1984

[54] TUBULAR ORGANIC PROSTHESIS

[75] Inventors: Hiroshi Mano; Toshisaburo Oga, both of Osaka, Japan

[73] Assignee: Sumitomo Electric Industries, Ltd., Osaka, Japan

[21] Appl. No.: 369,962

[22] Filed: Apr. 19, 1982

Related U.S. Patent Documents

Reissue of:

[64] Patent No.: 4,306,318
Issued: Dec. 22, 1981
Appl. No.: 84,325
Filed: Oct. 12, 1979

[30] Foreign Application Priority Data

Oct. 12, 1978 [JP] Japan ..... 53-125953

[51] Int. Cl.[3] ..... A61F 1/24
[52] U.S. Cl. ..... 3/1.4
[58] Field of Search ..... 3/1, 1.4

[56] References Cited

U.S. PATENT DOCUMENTS 3,105,492 10/1963 Jeckel ..... 3/1.4 X
3,479,670 11/1969 Medell ..... 3/1
3,490,975 1/1970 Lightwood et al. ..... 3/1.4 X
4,229,838 10/1980 Mano ..... 3/1.4

FOREIGN PATENT DOCUMENTS 2248015 5/1975 France ..... 3/1

*Primary Examiner*—Clifford D. Crowder
*Attorney, Agent, or Firm*—Sughrue, Mion, Zinn, Macpeak & Seas

[57] ABSTRACT

A tubular organic prosthesis comprising a porous tubing of polytetrafluoroethylene and elastic fibers provided helically on its outside surface.

14 Claims, 1 Drawing Figure

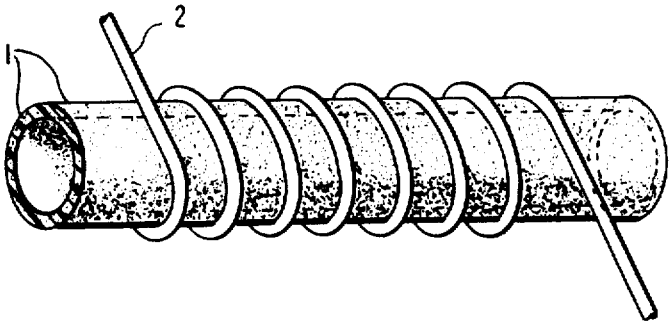
2
1

TUBULAR ORGANIC PROSTHESIS

Matter enclosed in heavy brackets [ ] appears in the original patent but forms no part of this reissue specification; matter printed in italics indicates the additions made by reissue.

BACKGROUND OF THE INVENTION

1. Field of the Invention

This invention relates to an improvement in and relating to a tubular organic prosthesis composed of a porous tubing of polytetrafluoroethylene (abbreviated "PTFE"), and is directed to increasing the strength of the tubing and its ability to connect with the tissues of a patient.

2. Description of the Prior Art

Many reports have been made heretofore to show that a porous tubing of PTFE produced by a stretching method can be clinically used as a tubular organic prosthesis, especially as a vascular prosthesis. Such a prosthesis is regarded as better than conventional prostheses made of knitted or woven fabrics. A PTFE tubing which has been subjected to a stretching treatment has a microstructure composed of very fine fibers and nodes connected to one another by the fibers. The diameters of the fibers vary depending on stretching conditions, and can be made much smaller than those of the fibers of the knitted or woven fabrics mentioned above. Moreover, since the pore diameter and porosity of the tubing can be varied freely, when it is used, for example, as an artifical vessel, it is pliable and scarcely permits formation of thrombus. The tubing also shows good formation of a pseudointima on the inner surface without any appreciable adverse effect on the surrounding tissues. Thus, the stretched tubing is regarded as one of the best prostheses for tubular organs.

The stretched PTFE tubing, however, has the disadvantage that when it is used as a tubular organic prosthesis and joined with the living body, the needle or suture tends to tear the tubing. This tearing frequently occurs in the axial direction of the porous PTFE tubing. Since this is due to the orientation of the fine PTFE fibers formed as a result of stretching, it can be reduced to some extent by biaxially stretching the tubing, namely stretching it in the axial direction and expanding its diameter, thereby to change the structure of the fine fibers to a radial orientation. A great improvement in strength, however, cannot be expected from this process alone. Furthermore, it is difficult for natural occlusion of suture holes to occur based on the elasticity of the porous PTFE tubing alone, and when it is used as an artificial vessel, bleeding from the suture holes is also a problem. Further, when it is sharply bent it buckles and cannot retain a cylindrical shape. This is also a drawback in practical application.

The present invention offers a solution to these problems in a junction operation.

SUMMARY OF THE INVENTION

It is an object of this invention to provide a tubular organic prosthesis comprising a porous PTFE tubing and elastic fibers provided helically on its outside surface.

Another object of this invention is to provide a tubular organic prosthesis which permits easy entry and attachment of the surrounding tissues to promote the assimilation of the prosthesis.

According to this invention, there is provided a tubular organic prosthesis comprising a porous tubing of polytetrafluoroethylene and elastic fibers provided helically on its outside surface.

In another aspect, the invention provides a process for producing a tubular organic prosthesis which comprises wrapping elastic fibers helically about the outside surface of a porous tubing of polytetrafluoroethylene, impregnating the resulting structure with a solvent capable of dissolving or swelling the elastic fibers to thereby bond them to the PTFE tubing, drying the structure, and then heat-setting.

BRIEF DESCRIPTION OF THE DRAWING

The FIGURE is a side view of the tubular prosthesis showing the essential elements thereof. Said tubular prosthesis is provided with a body of porous PTFE 1, which body is helically provided with elastic fibers upon its outer surface 2.

DETAILED DESCRIPTION OF THE INVENTION

As a result of providing elastic fibers helically on the outside surface of the porous PTFE tubing, the porous PTFE tubing of the present invention does not undergo tearing by a joining needle or suture. It also has the advantage that when the tubing together with the elastic fibers is sutured at the time of a junction operation, the holes left after joining are occluded by the elasticity of the fibers. Furthermore, since the elastic fibers are helically oriented, the tubing is pliable in the longitudinal direction, and even when it is sharply bent, it does not easily buckle. In addition, spaces for easy entry of the surrounding tissues of a patient are available on the outside surface of the tubing and this accelerate the assimilation of the porous PTFE tubing as an organic prosthesis.

The porous tubing of PTFE in accordance with this invention is produced by the method described in Japanese Patent Publication No. 13560/67 and, e.g., U.S. Pat. Nos. 3,953,566 and 3,962,153. A liquid lubricant is mixed with an unsintered powder of polytetrafluoroethylene and the mixture is extruded into a tubular form by a ram-type extruder. The PTFE used in this invention preferably has a molecular weight of $10^6$ to $10^7$. The tubing is stretched at least monoaxially after the liquid lubricant is optionally removed. Preferably, the tubing is stretched in the axial direction, and its diameter is expanded. The tubing is heated at a temperature above 327° C. which is the sintering temperature while fixing it in place to avoid shrinkage. Thus, the stretched and expanded structure is fixed and a tubing having increased strength is obtained. The resulting porous PTFE tubing has a microstructure composed of very fine fibers and nodes connected to one another by these fibers. Because the diameters and lengths of these fibers and the sizes and number of the nodes can be varied depending upon the stretching and sintering conditions, the pore diameter and porosity of the resulting porous tubing can be determined freely. It has been clinically confirmed that when this tubing is used as a vascular prosthesis, it suitably has an average pore diameter of about 2 μm to about 100 μm, a porosity of at least about 70%, and a wall thickness of about 0.3 to 1.0 mm.

In the microstructure of the porous PTFE tubing preferred in this invention, the fibers are distributed not unidirectionally but radially. This fibrous structure is obtained by biaxially stretching the PTFE tubing, namely by stretching it in the axial direction and expanding its diameter. Expansion of its diameter can be achieved by reducing the pressure on the outside surface of the tubing, or pressing its inside surface, or simultaneously performing these two procedures, while heating. Alternatively, the diameter of the tubing may be mechanically enlarged by passing an article of a suitable configuration through the inside of the tubing. Stretching of the tubing in the axial direction and expansion of its diameter are carried out simultaneously or successively, or may be carried out simultaneously with the final sintering step. The porous PTFE tubing obtained by the biaxial stretching method is more pliable and less prone to longitudinal tearing than a porous PTFE tubing stretched only in the axial direction because the fibers are distributed not only in the axial direction but radially in all directions. However, to perform a junction operation using this biaxially stretched porous PTFE tubing, more improvements in strength, natural occlusion of the suture holes, bending property, and the ability to connect with the tissues of a patient are desired.

In accordance with this invention elastic fibers are helically provided on the outside surface of the porous PTFE tubing to solve the aforesaid problems.

The elastic fibers are fibers produced from at least 50% elastomer. They include polyurethane fibers and fibers from various rubbers (so-called rubber yarns), e.g., silicone rubbers, fluorine rubbers, acrylic rubbers, natural rubber, etc. Examples of non-elastomers which may be present in combination with the elastomers include polyamides, polyesters, polypropylenes, etc. The elastic fibers used in this invention are described in detail below with reference to polyurethane fibers which constitute a preferred embodiment of the present invention. Substantially the same description will apply to other elastic fibers.

Preferably fibers are selected and wrapped around the prosthesis to give it a suture tear resistance of at least 300 g/ply. The polyurethane elastic fibers are made from an organic diisocyanate and a polyether or polyester and are characterized by their elasticity. Polyurethane fibers normally used for apparel are also suitable for the purposes of this invention. Polyurethane elastic fibers of the polyether type are especially suitable for organic prostheses.

The fibers may be in the form of monofilaments or multifilaments. Not only bare yarns of polyurethane but also processed or modified yarns can be used to achieve the objects of this invention. Commercially available processed yarns include covered yarns having other fibers wrapped thereabout, core spun yarns having polyurethane fibers as a core, ply yarns, etc. All of these yarns can be used in this invention. The polyurethane elastic yarns usually have a tensile strength of about 1 to 1.5 g/denier (ASTM D-638) and those having a size of about 150 denier to about 5,000 denier are effective.

To provide the elastic fibers helically on the outside surface of the porous PTFE tubing, the fibers are first helically wrapped about the outside surface of the tubing. The fibers may be wrapped in close contact with one another, or at some interval, preferably not exceeding the diameter of the prosthesis. A suitable thickness of the fiber wrapping ranges from about 0.05 mm to about 1 mm.

After wrapping, the fibers are impregnated with a solvent capable of dissolving or swelling the elastic fibers to dissolve the elastic fibers partly and bond them to the PTFE tubing. Suitable solvents for the polyurethane elastic fibers include phenol, m-cresol, benzene, toluene, formic acid, tetrahydrofuran, N,N-dimethylformamide and N,N-dimethylacetamide. The structure impregnated with the solvent is dried, and then heated at a suitable temperature to heat-set it. This heat-setting relaxes the residual stress of the helically wrapped elastic fibers, and sets their configuration. The heat-setting temperature and time are determined according to the material of the elastic fibers. In the case of polyurethane elastic fibers, heat-setting is usually carried out at a temperature of about 120° to 230° C. for a period of 1 to 60 minutes. Heating may be effected in air or with steam or the like.

The tubular organic prosthesis of this invention described hereinabove is very useful as an artificial vessel, but can also be used for the prosthesis of other tubular organs including the esophagus, trachea, biliary duct, ureter, and urethra.

The following Examples illustrate the present invention more specifically. It should be understood that the scope of the invention is not limited by these Examples.

EXAMPLE 1

One hundred parts by weight of fine PTFE powder, Polyflon F-104 (a trademark for a product of Daikin Kogyo Co., Ltd.), was mixed uniformly with 29 parts by weight of a liquid lubricant (Deobase). The mixture was pre-formed under pressure, and extruded by a ram-type extruder into a tubing having an inside diameter of 3.0 mm and an outside diameter of 4.5 mm. The tubing was dipped in trichloroethylene to extract and remove the liquid lubricant, and then stretched 200% in the axial direction of the tubing while it was heated at about 250° C. The stretched tubing was then heated at 350° C. while reducing the pressure on the outside surface of the tubing to expand its diameter and simultaneously sinter the tubing. The tubing obtained was a porous tubing having an inside diameter of 4.0 mm, and outside diameter of 4.9 mm, and a porosity of 79%.

A stainless steel rod having a diameter of 4.0 mm was inserted in the porous PTFE tubing, and elastic polyurethane multifilaments having a size of 1,120 denier were densely wrapped helically about the outside surface of the tubing. The filaments were fixed at both ends, and impregnated with tetrahydrofuran to bond them. The resulting structure was dried and heated at 170° C. for 10 minutes to heat-set the fibers. The resulting tubing did not deform even when the stainless steel rod was withdrawn. It was pliable and had high flexibility. When a stainless steel wire having a diameter of 0.40 mm was inserted in a loop-like configuration into the wall of the tubing at 5 mm from one end of the tubing, and pulled in the axial direction of the tubing at a speed of 50 mm/min., tearing occurred in the tubing under a load of 1,250 g which is much larger than the load (180 g) under which tearing occurred in the tubing without the elastic fibers. Holes left after inserting a surgical suturing needle were naturally occluded by the elasticity of the elastic fibers. Thus, the resulting product had various superior characteristics as a tubular organic prosthesis.

EXAMPLE 2

Elastic polyurethane multifilaments having a size of 2,240 denier were wrapped helically at intervals of 0.5 mm about the outside surface of the same porous PTFE tubing as used in Example 1, and treated in the same way as in Example 1. The load under which tearing occurred in the resulting tubing was 860 g. Thus, the product had superior characteristics as a tubular organic prosthesis as in the case of the tubing obtained in Example 1.

While the invention has been described in detail and with reference to specific embodiments thereof, it will be apparent to one skilled in the art that various changes and modifications can be made therein without departing from the spirit and scope thereof.

What is claimed is:

1. A tubular organic prosthesis comprising a porous tubing of polytetrafluoroethylene and elastic fibers provided helically on its outside surface.

2. The prosthesis of claim 1, wherein said polytetrafluoroethylene tubing has a microstructure composed of fibers and nodes connected to one another by said fibers, said fibers being radially distributed.

3. The prosthesis of claim 1, wherein said elastic fibers are made from polyurethane.

4. The prosthesis of claim 3, wherein said polyurethane is a polyether polyurethane.

5. The prosthesis of claim 4, wherein said prosthesis has a suture tear resistance of about 300 g/ply or more.

6. The prosthesis of claim 1, wherein said elastic fibers are rubber yarns.

7. The prosthesis of claim 1, wherein said fibers have a denier of about 150 to about 5,000.

8. The prosthesis of claim 1, wherein said fibers have a tensile strength of about 1 g/denier.

9. The prosthesis of claim 1, wherein said PTFE tubing has a porosity of at least about 70%.

10. The prosthesis of claim 1, wherein said PTFE tubing has a wall thickness of about 0.3 to 1.0 mm.

11. The prosthesis of claim 1, wherein said PTFE tubing has an average pore diameter of about 2 μm to about 100 μm.

12. The prosthesis of claim 1, wherein said prosthesis has a suture tear resistance of about 300 g/ply or more.

13. The tubular organic prosthesis of claim 1, wherein said tubular organic prosthesis is a vascular prosthesis.

14. The prosthesis of claim 13, wherein said prosthesis has a suture tear resistance of about 300 g/ply or more.

* * * * *